(12) United States Patent
Judge et al.

(10) Patent No.: US 6,401,138 B1
(45) Date of Patent: Jun. 4, 2002

(54) INTERFACE FOR PATIENT CONTEXT SHARING AND APPLICATION SWITCHING

(75) Inventors: Frank Judge, Lawrence; Howard Sumner, Bedford; Andrew Scott Braunstein, Brookline, all of MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 47 days.

(21) Appl. No.: 08/739,087

(22) Filed: Oct. 28, 1996

(51) Int. Cl.⁷ ................................................. G06F 9/54
(52) U.S. Cl. ...................... 709/328; 709/108; 709/313; 709/318; 705/2; 705/3
(58) Field of Search ................................. 395/680, 684; 709/300, 108, 302, 318, 328; 705/2, 3, 1, 500

(56) References Cited

U.S. PATENT DOCUMENTS

| | | | | |
|---|---|---|---|---|
| 5,226,117 A | * | 7/1993 | Miklos | 345/853 |
| 5,345,551 A | * | 9/1994 | Shelley et al. | 345/804 |
| 5,448,738 A | * | 9/1995 | Good et al. | 709/329 |
| 5,485,617 A | * | 1/1996 | Stutz et al. | 709/315 |
| 5,530,865 A | * | 6/1996 | Owens et al. | 709/313 |
| 5,546,580 A | * | 8/1996 | Seliger et al. | 707/8 |
| 5,592,664 A | * | 1/1997 | Starkey | 707/1 |
| 5,664,207 A | * | 9/1997 | Crumpler et al. | 345/733 |
| 5,666,492 A | * | 9/1997 | Rhodes et al. | 705/2 |
| 5,752,159 A | * | 5/1998 | Faust et al. | 725/105 |
| 5,835,089 A | * | 11/1998 | Skarbo et al. | 345/751 |
| 5,862,377 A | * | 1/1999 | Lee | 709/329 |
| 5,946,659 A | * | 8/1999 | Lancelot et al. | 705/2 |

FOREIGN PATENT DOCUMENTS

EP 0713178 A1 * 5/1996 ............. G06F/9/46

OTHER PUBLICATIONS

Douglass, A. Young. "XWindow Systems Programming and Applications with Xt", 1989.*

Stinson, Craig. "Running Windows 3.1", 1992.*

(TANG) Tang, P.C. "Semantic integration of information in a physician's workstation". abstract, Feb. 1994.*

(MICROSOFT) Microsoft Press. "OLE 2 Programmer's Reference" vol. One, p. 15, 1994.*

(PERSON) Person, Ron. "Using Windows 95" pp. 24, 60, 1995.*

Arora Shail, "Object–Oriented Technology for Health Care and Medical Information Systems", Oct. 1995.*

Microsoft Online Documentation. "Contrasting Linked and Embedded Objects".*

"Semantic integration of information in a physician's workstation", Tang, et al.; International Journal of Bio–Medical Computing 35 (1994) 47–60.

* cited by examiner

Primary Examiner—St. John Courtenay, III
Assistant Examiner—Lewis A. Bullock, Jr.

(57) ABSTRACT

In a medical information system, a facility is provided so that different application programs can share information about their current state, so that a user of these applications can move more efficiently among them. This facility includes a patient context interface (PCI) that each application can access by means of an application programming interface (API). This API provides mechanisms by which applications can register their identity and their interest in certain types of data and events. The PCI stores data received from applications for sharing with other applications, and the PCI notifies certain applications of events received from other applications. In operation, an application that is used to review data for a patient stores (in the PCI) an identification of the patient whose data is currently being reviewed, and another application retrieves (from the PCI) that patient identification so that it can automatically present that patient's data when the user switches to that application. In addition, an application can retrieve the names of other applications and can present these names to a user, so that the user can switch to one of those applications to review data that is related to data that the user is reviewing in the first application (e.g., data about the same patient).

6 Claims, 15 Drawing Sheets

INTERFACE FOR PATIENT CONTEXT SHARING AND APPLICATION SWITCHING

FIELD OF THE INVENTION

The present invention relates to improvements in the usability of medical information systems, and in particular to a facility that supports users switching among different application programs such that these applications retain the same patient context.

BACKGROUND

Computer programs have been developed to support many different aspects of the healthcare delivery system (e.g., clinical information systems, patient monitoring systems, decision support systems, hospital administration systems). The resulting medical information system is a diverse array of relatively independent programs: programs developed at different times, programs developed to address different problems, programs developed by or for people with different areas of expertise. In evaluating any particular patient situation, a user of such a composite medical information system may need to review data about a single patient using more than one program.

Although programmers have developed mechanisms for sending data from one program to another, for coordination of the displays in separate windows of one program, for event-driven message passing between programs, and other such techniques, the usability of composite medical information systems continues to suffer from the separateness of the programs that make up such systems. Because of the independent nature of such programs, one program does not have the benefit of the context of another of the programs. For example, a clinician must go through similar (seemingly redundant) introductory steps (such as to identify and locate a particular patient's record) with each program.

SUMMARY OF THE INVENTION

According to the present invention, a patient context interface (PCI) provides services to a plurality of programs within a composite medical information system. The PCI provides these services by means of an application programming interface (API).

These services include the following: registering application programs using the PCI (and permitting applications to learn about other applications that have registered to use the PCI); registering application programs for particular events, such as a change in an item of stored patient context information, (and sending notifications to such applications when an update to such stored item occurs); storing patient context information received from application programs (and providing this stored information to other applications upon request). These services permit an application to send various types of events to all other programs that have registered for that type of event. Further, these services permit one application to send a focus change event to a specified second application and permit the second application to read patient context information so that the second application display's data coordinated with the first application (for example, the second application can automatically retrieve data for the same patient whose data is being displayed by the first application).

With the PCI, each of a plurality of applications can be written to work with a single, common interface and yet share patient context with a plurality of other applications. In addition, using the PCI, an application can identify (on a real-time basis) other medical applications, can present to a user of the system a list of such applications from which the user can select an application, and can cause the user interface focus to switch to that selected application.

Thus, the PCI permits medical applications to share patient context information, such as patient identifications (e.g., the clinician is now looking at data for the patient with medical record number X), time periods (e.g., the clinician is now looking at last week's data), body system (e.g., the clinician is now looking at data relating to the functioning of the patient's neural system), disease (e.g., the clinician is now looking at data indicative of the progress of a particular one of the patient's physiological disorders), department (e.g., the clinician is now looking at data from the cardiology department).

BRIEF DESCRIPTION OF THE DRAWING

The invention is pointed out with particularity in the appended claims. The above and other advantages of the invention may be better understood by referring to the following detailed description in conjunction with the drawing, in which:

DETAILED DESCRIPTION OF AN ILLUSTRATIVE EMBODIMENT

Figure 1:
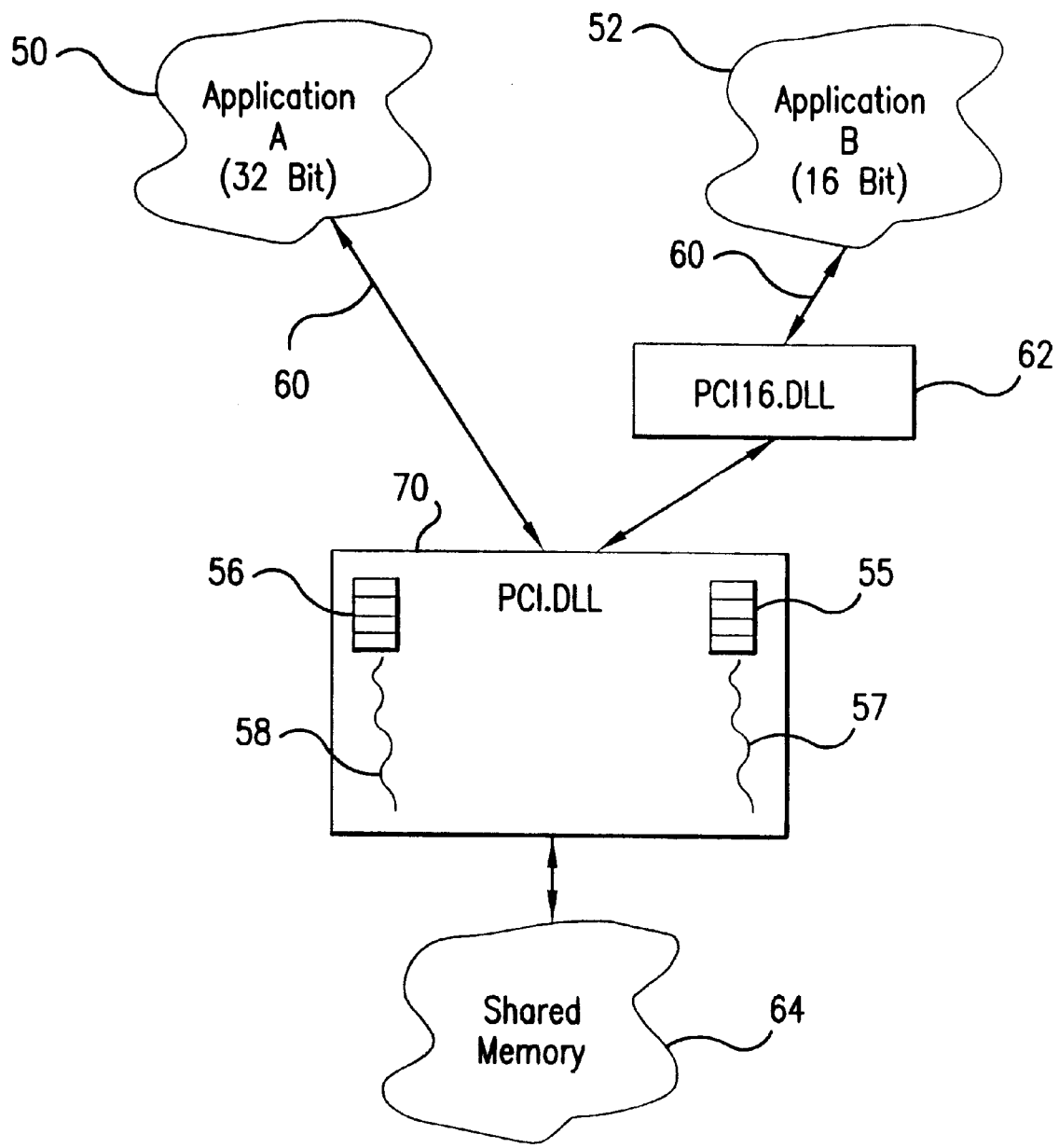
FIG. 1 illustrates some internal aspects of a patient context interface (PCI) according to the present invention and how the PCI interacts with application programs.

An illustrative embodiment of the invention is described below by (1) describing a design for a application programming interface (API) for a patient context interface (PCI), (2) describing an implementation of the services to support that API, and (3) describing how applications are built to take advantage of the PCI. Use of the PCI by an application program is illustrated by discussion of the CareVue clinical information system from Hewlett-Packard Company. Other healthcare information applications such as patient scheduling systems and medical data archive systems are also good candidates for using the PCI.

1 The PCI API

Application programs (often simply "applications") interact with the PCI through an application programming interface (API)—in particular, the applications make calls to a set of functions that invoke computer program code in the PCI's dynamic link library (DLL). The PCI API includes the following function calls (described in greater detail below):

PCI_RegisterApplication(name)

PCI_RegisterData(data)

PCI_RegisterEvent(event, clientDatap, notifyCallback)

PCI_RegisterEventW(event, window, uMessage)
PCI_Store(data)
PCI_Notify(event, hndl)
PCI_RetrieveAppls(namev, hndlv, count)
PCI_Retrieve(data)

1.1 PCI-RegisterApplication( )

The PCI_RegisterApplication( ) function registers an application with the PCI. This function must be called prior to an application calling any other PCI function. The name argument should be unique across all applications using the PCI. Another application may retrieve this name via the PCI_RetrieveAppls( ) function, and display the name to users (for example, to permit users to select an application to which they want to switch).

Function Declaration
    PCI_ReturnType PCI_RegisterApplication( char *name );
Parameters
char *name
    Required parameter to identify the application to the PCI. Maximum application name length is PCI_APPLNAMEMAX characters, including the NULL terminator.
Return Value
    If the function succeeds, the return values is PCI_SUCCESS.
    If the name is NULL, the return value is PCI_INVALIDARGS.
    If the application is already registered with the PCI, the return value is PCI_DUPLICATEAPP.
    If more than the maximum number of applications are registered with the PCI, the return value is PCI_MAXREACHED.

1.2 PCI_RegisterData( )

The PCI_RegisterData( ) function registers a data type with the PCI so an application may store and retrieve that type of data in the future. This function must be called prior to calling PCI_Store( ) or PCI_Retrieve( ).

Function Declaration
    PCI_ReturnType PCI_RegisterData( PCI_Data data );
Parameters
PCI_Data data
    A struct (C language data structure) containing:
    PCI_DataType dataId;
    PCI_Any datap;
    PCI_DataSz sz;
    The dataId value must be unique across all applications using the PCI, and identical in those applications wishing to share the data value. The datap value is a pointer to a buffer containing the initial value of the data type. Note it is permissible for this value to be NULL initially. The sz value identifies the size of the data being registered.
Return Value
    If the function succeeds, the return value is PCI_SUCCESS.
    If the data argument is invalid, the return value is PCI_INVALIDARGS.
    If the application is not registered with the PCI, the return value is PCI_NOTREGISTERED.
    If more than the maximum number of data types are registered with the PCI, the return value is PCI_MAXREACHED.

1.3 PCI_RegisterEvent( ) and PCI_RegisterEventW( )

The PCI_RegisterEvent( ) and PCI_RegisterEventW( ) functions register an-event type with the PCI so an application may notify the PCI of that type of event and/or be notified by the PCI when another application notifies the PCI that such an event has occurred. Prior to calling PCI_Notify( ), one of these two functions must be called by each application wishing to use the event type. When an event occurs, applications registered using PCI-RegisterEvent( ) function are notified by a callback mechanism, and applications registered using this PCI_RegisterEventW( ) function are notified by a Microsoft Windows message (in particular, the message specified in this function call is posted to the message queue for the particular window specified in this function call). The PCI_RegisterEventW( ) function is used by 16-bit applications; 32-bit applications may use either of the two even registration functions.

Although the PCI_Notify( ) function initiates certain events, there are events that are initiated by the PCI itself. For example, the updating of a data value is an event. Any application registered for a type of data may also register for the corresponding data change event, so that the application will be notified by the PCI when that data item is updated. There are other events initiated by the PCI: registration of an event or data is itself an event; registration of an application is an event; and occurrence of any event is an event. While some of these events are primarily of use for debugging, any application may register to receive these events, in the same way that applications register to receive events initiated by PCI_Notify( ).

A focus change event is another pre-defined event type; however, these events are not initiated by the PCI itself. A focus change event is used to permit application switching, as described below in section 3.3 "Use of the PCI API".

Function Declaration
    PCI_ReturnType PCI_RegisterEvent ( PCI_Event event, PCI_Any clientDatap, PCI_InterfaceCB notifyCallback );
    PCI_ReturnType PCI_RegisterEventW ( PCI_Event event, PCI_HWND window, PCI_UMsg uMessage );
Parameters
PCI_Event event
    A struct containing:
    PCI_EventType eventId;
    PCI_DataType optDataId;
    The eventId value must be unique across all applications using the PCI, and identical in those applications wishing to share the event. The optDataId may be used to link an event identified by eventId to a type of data, such as the following example: a particular eventID could indicate that there has been a change in one of several possible data items; the optDataId parameter would indicate which of the data items had been changed.
PCI_Any clientDatap
    Application specific data to be passed to the callback function when the event occurs. Because the data is passed by pointer, the address must be valid for as long as the event is to occur.
PCI_InterfaceCB notifyCallback
    A function to be called by the PCI when the event occurs. The callback function must be of the form:
    foo( PCI_Event eventId, PCI_Any *clientDatap )
where the value of eventID has already been registered with the PCI by this application, and PCI_Any *clientDatap is application specific data provided by the application as described above. This callback function must be NT thread safe because it is being called in a separate NT thread when the event occurs.
PCI_HWND window
    A Microsoft Windows handle for the window that is to receive the message when the event occurs.

PCI_UMsg uMessage

A valid Microsoft Windows message (preferably in the WM_USER range) to be posted to the above identified window when the event occurs.

Return Value

If the function succeeds, the return value is PCI_SUCCESS.

If the event argument is invalid, the return value is PCI_INVALIDARGS.

If the application is not registered with the PCI, the return value is PCI_NOTREGISTERED.

If more than the maximum number of event types are registered with the PCI, the return value is PCI_MAXREACHED.

1.4 PCI_Store( )

The PCI_Store( ) function allows applications to store data in the PCI by copying the data from an application's buffer. The PCI does not itself interpret the content of the data; it is the applications sharing the data that give particular meaning to the data. Any applications registered for a particular type of data may update the value of that data; it is the responsibility of each such application to assure that the same dataId and sz are used.

Because the data is not interpreted by the PCI, the applications that store and/or retrieve a particular data type must store and retrieve that data in a common format (unless the format is self-identifying, permitting each application to identify the format of stored data, so that the application can convert the data if necessary). For example, applications sharing text should store the text in the PCI using a character set that can be interpreted by all of those applications.

Ideally, applications using the PCI should update the patient context information whenever the information changes, such as when a user seelets a new patient; however, this may not always occur (e.g., due to a design limitation or error in the application).

Function Declaration

PCI_ReturnType PCI_Store( PCI_Data data );

Parameters

PCI_Data data

A struct containing:

PCI_DataType dataId;

PCI_Any datap;

PCI_DataSz sz;

The dataId value must be unique across all applications using the PCI, and identical in those applications wishing to share the data value. The datap value is a pointer to a buffer containing the value to be stored. It is not permissible for this value to be NULL for a data store operation. The sz value identifies the size of the data to be retrieved.

Return Value

If the function succeeds, the return value is PCI_SUCCESS.

If data.datap is NULL or data.sz is greater than the registered size, the return value is PCI_INVALIDDATA.

If the application or the dataId is not registered with the PCI, the return value is PCI_NOTREGISTERED.

1.5 PCI_Notify( )

The PCI_Notify( ) function is used to notify the PCI that an event has occurred. Upon such notification, the PCI notifies either all or a selected one of those applications that have registered the corresponding event type (except that the application calling this function is not notified about the event). Applications that have registered by using PCI_RegisterEvent( ) are notified by executing their callback functions; applications that have registered by using PCI_RegisterEventW( ) are notified by sending a Microsoft Windows message. This function returns when all interested applications have been notified, but does not wait for those applications to process the event.

Function Declaration

PCI_ReturnType PCI_Notify( PCI_Event event, PCI_ApplHandle hndl );

Parameters

PCI_Event event struct containing:

PCI_EventType eventId;

PCI_DataType optDataId;

The eventId value must be unique across all applications using the PCI, and identical in those applications wishing to share the event. The optDataId may be used to link the event to a data ID, as described above in connection with the PCI_RegisterEvent( ) function.

PCI_ApplHandle hndl

Identifies the application to be notified. All applications registering this event may be notified by setting hndl to PCI_ALLAPPLICATIONS. Valid handles may be obtained from the PCI via the PCI_RetrieveAppls( ) function. A target application will only be notified if it is both registered with the PCI and registered for this event.

Return Value

If the function succeeds, the return values is PCI_SUCCESS.

If the event argument is invalid, the return value is PCI_INVALIDARGS.

If the hndl argument is invalid, the return value is PCI_INVALIDHNDL.

If the application or the event is not registered with the PCI, the return value is PCI_NOTREGISTERED.

1.6 PCI_RetrieveAppls( )

The PCI_RetrieveAppls( ) function is retrieves a list of names and PCI application handles for all applications registered with the PCI. The names returned are the names each application registered with the PCI (using PCI_RegisterApplication( ) ). PCI_ApplHandles are guaranteed to be valid for as long as the application described by the handle is registered with the PCI. The PCI_ApplHandles returned may be used with the PCI_Notify( ) function to notify a particular application about an event.

Function Declaration

PCI_ReturnType PCI_RetrieveAppls( char namev, PCI_ApplHandle hndlv, PCI_ApplIndex *count );

Parameters char **namev

An array of pointers to buffers in which application names are to be stored. The size of the array should be *count long; the maximum size of each buffer should be PCI_APPLNAMEMAX long, including the NULL character.

PCI_ApplHandle **hndlv

An array of pointers to buffers in which the PCI application handles are to be stored. The size of the array should be *count long.

PCI_ApplIndex *count

A pointer to number of elements in the above arrays. On return this value will be changed to number of elements actually returned by the PCI. The maximum count allowed is PCI_APPLMAX.

Return Value

If the function succeeds, the return values is PCI_SUCCESS.

If any argument is NULL or *count is 0, the return value is PCI_INVALIDARGS.

If the application is not registered with the PCI, the return value is PCI_NOTREGISTERED.

If *count is less than the actual number of applications registered with the PCI, as many as possible are filled in to the above arrays and the return value is PCI_BUFFER2SMALL.

1.7 PCI_Retrieve( )

The PCI_Retrieve( ) function retrieves data from the PCI by copying the data to an application's buffer. The same data may be retrieved by any number of the applications that have registered for that particular type of data. The PCI does not itself interpret the content of the data; it is the applications sharing the data that give particular meaning to the data. It is the responsibility of the applications sharing data through the PCI to be sure to use the same dataId and sz for each type of data being shared.

Function Declaration

PCI_ReturnType PCI_Retrieve( PCI_Data data );

Parameters

PCI_Data data

A struct containing:

PCI_DataType dataId;

PCI_Any datap;

PCI_DataSz sz;

The dataId value must be unique across all applications using the PCI, and identical in those applications wishing to share the data value. The datap value is a pointer to a destination buffer to which the data is to be copied. It is not permissible for this value to be NULL for a retrieve. The sz value identifies the size of the data to be retrieved.

Return Value

If the function succeeds, the return values is PCI_SUCCESS.

If data.datap is NULL, the return value is PCI_ERROR.

If the application or the dataid is not registered with the PCI, the return value is PCI_NOTREGISTERED.

If data.sz is less than the size of the data stored in the PCI, the value is not retrieved and the return value is PCI_BUFFER2SMALL.

2 PCI Internals

The illustrative PCI is implemented in the C++ programming language and runs under Microsoft Windows NT (a product of Microsoft Corporation). Because the design was developed using object oriented methodologies, the following description uses class hierarchy and object event diagrams. The executable program code implementing the PCI is stored on magnetic disk and loaded into RAM for execution. Alternatively, it could be stored in other types of computer-readable media.

Figure 2:
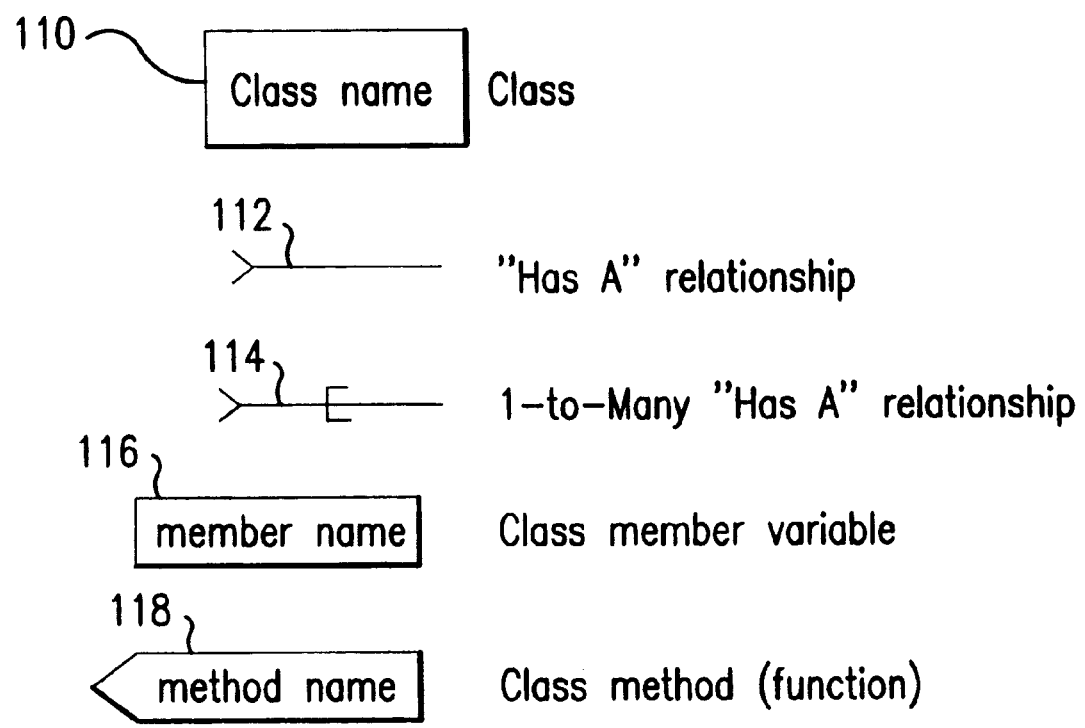
FIG. 2 illustrates symbols used in the class diagrams of FIGS. 3–7.

The object oriented class diagrams shown in the figures are based on the Rumbaugh object oriented design diagramming technique. These diagrams use the following conventions. The large rectangles (such as 110, in FIG. 2) represent classes or types. Connections between these boxes such as 112 represent "has a" relationships. Connections with an U-shaped symbol (such as 114) represent one-to-many "has a" relationships. Small rectangles (such as 116) represent class member variables. Small 5-sided boxes (such as 118) represent class methods (i.e., functions).

2.1 Architecture

FIG. 1 shows two applications (illustrative application A 50 is a 32-bit application, and one illustrative application B 52 is a 16-bit application); these two are illustrative only, as there may be any number (limited only by constraints imposed by a particular implementation) of applications, and these may all be 16-bit or all 32-bit applications, or any mixture of 16-bit and 32-bit applications.

Applications interact with the PCI through the PCI API 60, which they access by calling the functions described above. These functions invoke code in one or both of two NT dynamic link libraries (DLLs). If the application is a 32-bit native NT application, it uses the NT native PCI.DLL 70, which is a 32-bit dynamic link library; if the application is 16-bit application (i.e., Microsoft Windows 3.1 applications) it uses the PCI 16.DLL 62, which acts as an interface to the 32-bit PCI.DLL, as is illustrated in FIG. 1. The PCI 16.DLL converts all application data passed to the PCI from 16-bit to 32-bit values, as well as from the 16-bit segmented memory model to the 32-bit flat memory model. Under NT this conversion is known as thunking, and the PCI16.DLL interface is known as a thunking layer.

The PCI's data sharing mechanism is implemented as shared memory 64. Each application registering with the PCI gains access to the shared memory 64 through the PCI functions PCI_Retrieve( ) and PCI_Store( ).

Event notification is implemented as a separate event queue (such as the event queue 56 for application A and event queue 55 for application B) and a separate NT thread (such as the event thread 58 for application A and event thread 57 for application B) for each application registered with the PCI to receive one or more types of events. When an application calls PCI_Notify( ), new events are placed on the event queues for each application to be notified. Each thread corresponding an application to be notified is signaled to read the event off its queue and notify its corresponding application. The notification occurs in one of two ways depending upon whether the application to be notified registered using PCI_RegisterEvent( ) or PCI_RegisterEventW( ): in the first case (32-bit applications), the application is notified calling the callback function provided by the application; in the second case (16-bit applications; and, 32-bit applications that chose, by using PCI_RegisterEventW( ) function, to be notified by a Microsoft Windows message), the thread posts a Microsoft Windows message to the applications message queue.

2.2 Classes

Figure 3:
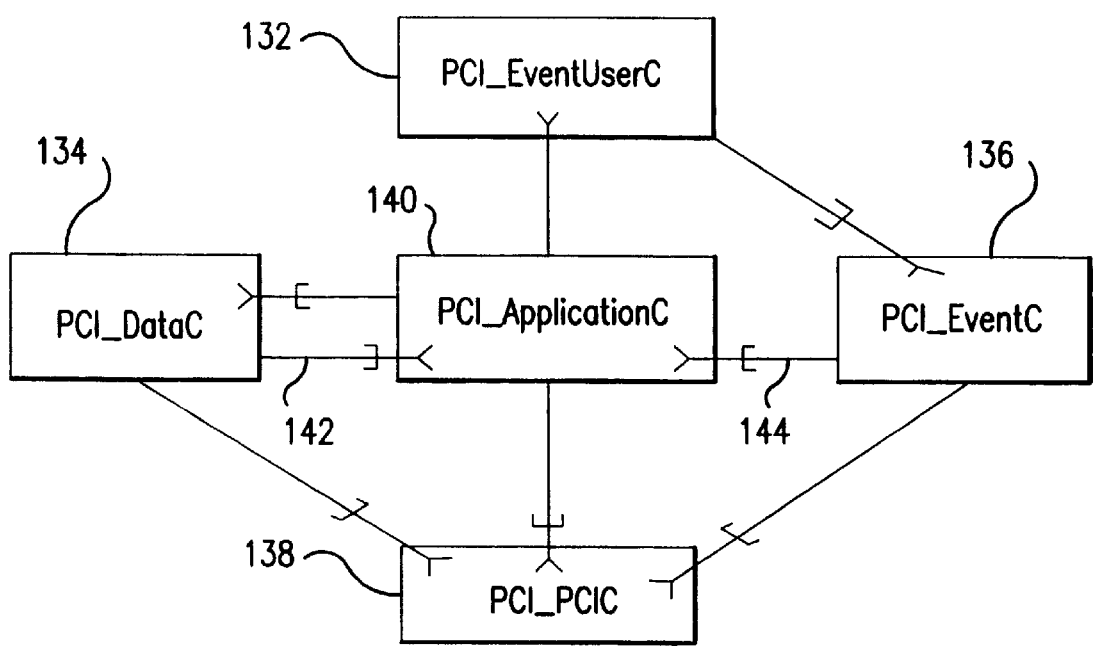
FIG. 3 illustrates relationships among the major classes of objects in an illustrative implementation of the PCI.

The illustrative embodiment of the PCI is built using C++ objects that model different entities, such as applications, events, and data. The major object classes are as follows: PCI_PCIC 138, PCI_ApplicationC 140, PCI_EventC 136, PCI_EventUserC 132, PCI_DataC 134, PCI_QueueC, PCI_AllocatorC. FIG. 3 shows how these classes are related to each other. (Note that two of the "has-a" relationships illustrated in FIG. 3, 142 and 144, are intended primarily for debugging.)

2.2.1 PCI_PCIC

Figure 4:
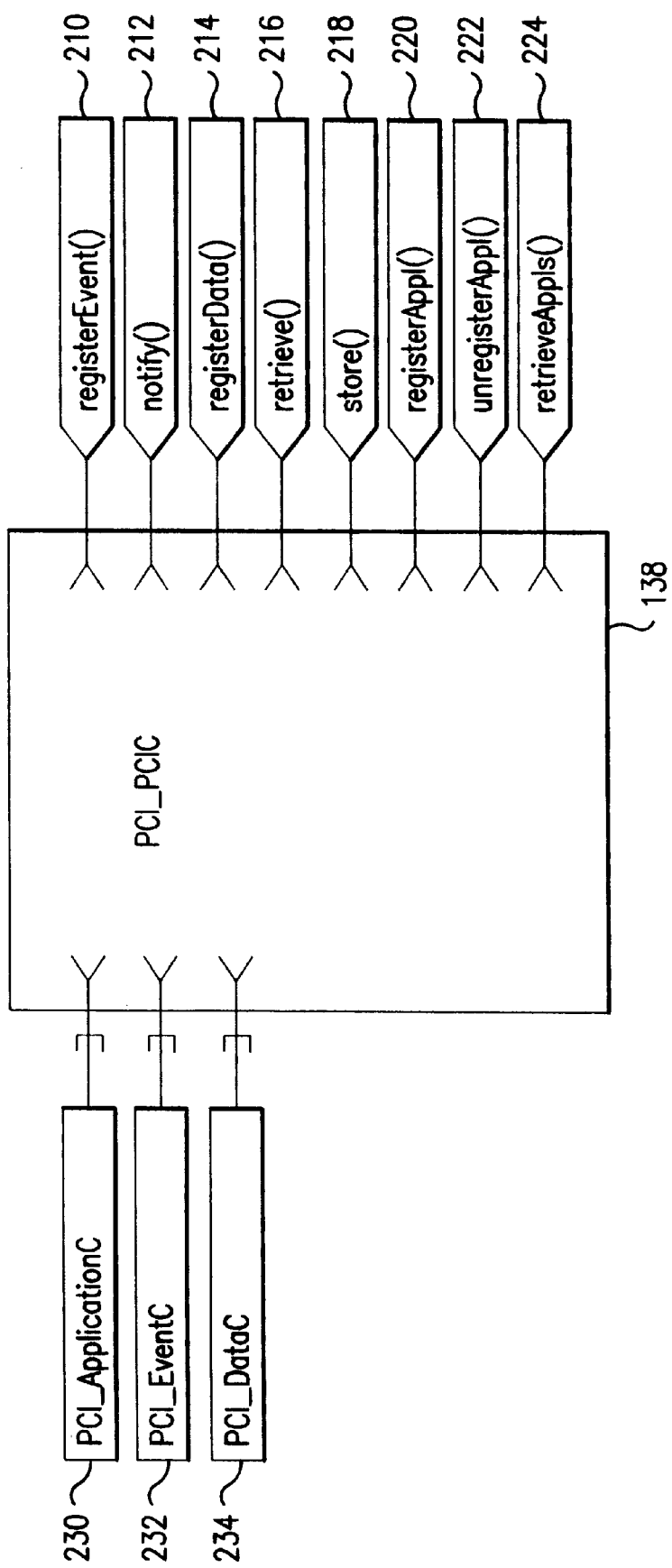
FIG. 4 illustrates the PCI_PCIC object class, in particular, class methods and members.

The PCI_PCIC class 138 is illustrated in FIG. 4. A single object of class PCI_PCIC represents the overall PCI. The function calls that applications make to the PCI are directed to this single PCI_PCIC object. To handle these function calls, the PCI_PCIC class has a method corresponding to each such finction call (the name of each method is similar to the name of the corresponding function call): registerAppl( ) 220, unregisterAppl( ) 222 (in the illustrative implementation this method is used internally by the PCI, but is not directly available in the API; a function call corresponding to this method could be added to the API), registerData( ) 214, registerEvent( ) 210 (including versions for each of the two event registration function calls), store( ) 218, notify( ) 212, retrieveAppls( ) 224, and retrieve( ) 216.

This PCI_PCIC object includes an array of application objects 230, an array of data objects 234, and an array of event objects 232. When an application registers with the PCI, a PCI_ApplicationC object is created and a reference to it is added to an array of such references 230 in the PCI_PCIC object 138. Likewise, when data and events are registered with the PCI, PCI_DataC and PCI_EventC objects are created and references are added to corresponding arrays 234 and 232. The PCI_PCIC object then uses these objects in handling the function calls that make up the PCI API.

2.2.2 PCI_ApplicationC

Figure 5:
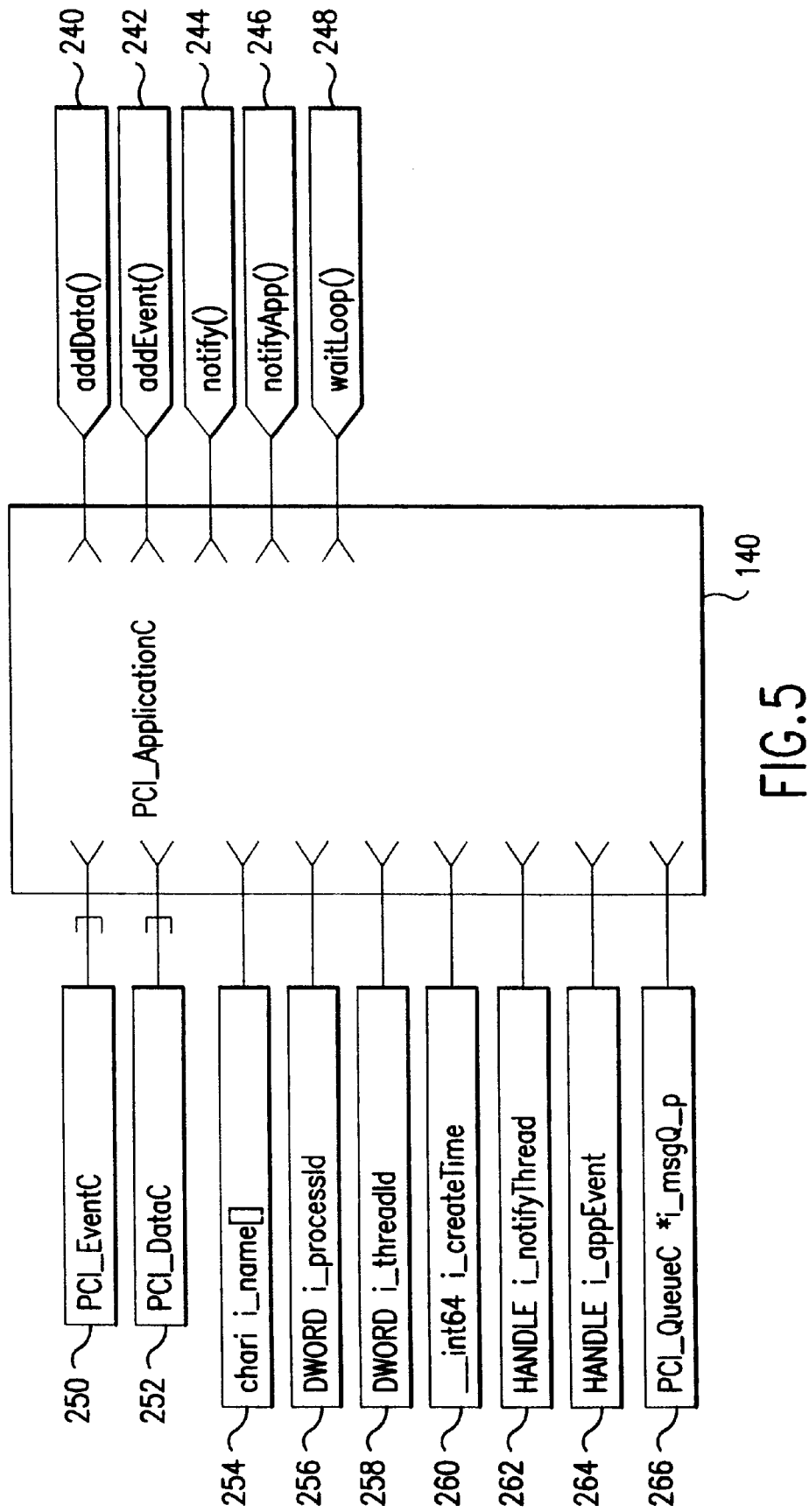
FIG. 5 illustrates the PCI_ApplicationC object class, in particular, class methods and members.

The PCI_ApplicationC class 140 is illustrated in FIG. 5. An object of class PCI_ApplicationC is created for each application that registers with the PCI (i.e., calls the PCI_RegisterApplication( ) function).

In order to identify the application with which each PCI_ApplicationC object is associated, the name of the application (as specified in the function call) is stored in the i_name member 254 of the object, and the NT process ID, the NT thread ID, and the NT process create time (the values required to uniquely identify an application under NT) are stored in the i_processId 256, i_threadId 258, and i_createTime 260 members, respectively.

When an object of class PCI_ApplicationC is created, a thread is created for use in notifying the application of events for which it is registered. (Alternatively, this thread could be created at another time, such as when the application registers to be notified of some particular type of event.) The NT thread ID for this thread is stored in the i_notifyThread member 262. When this thread starts, it executes the waitLoop( ) method 248, which waits for the thread to be signaled that an event has been placed on its event queue; such event is an object of class PCI_QueueC that is stored in the i_msgQ_p member 266 of the application object. A conventional NT event object is created to signal this thread when an event is placed on its queue; the handle of this NT event object is stored in the i_appEvent member 264.

When an application registers a data type, the addData( ) method 240 is invoked. This causes creation of a new PCI_DataC object, unless one already exists for the type of data that the application is registering. To implement the 'has-a' relationship from the PCI_DataC objects to the PCI_ApplicationC objects, a reference to the registering PCI_ApplicationC object is added to an array of such references (278 in FIG. 6) in the newly created or existing PCI_DataC object.

When an application registers an event type, the addevent( ) method 242 is invoked. The effect is similar to invoking addData( ) 240, except that an object of class PCI_EventUserC is interposed between the PCI_EventC object and the PCI_ApplicationC object, as further described below. When an application registers an event, a PCI_EventUserC object is created; because each PCI_EventUserC object is unique to a single PCI_ApplicationC object, the appropriate PCI_EventUserC will not already exist. A reference to this PCI_EventUserC object is added to the array of such references (not show separately, but illustrated by the relationship 281 in FIG. 7) in the PCI_EventC object, and a reference to the PCI_ApplicationC object is stored in the PCI_EventUserC object (in variable i_appl_p 298 in FIG. 7).

Also, for debugging purposes, a reference to the PCI_EventC or PCI_DataC object for the event type or data type being registered is added to the corresponding array (one for data types 252 and one for event types 250) in the PCI_ApplicationC object. These application-to-data and application-to-event 'has-a' relationships (142 and 144 in FIG. 3) are not needed for executing the PCI functionality; however, they can be useful when debugging PCI-related program code.

When an application calls the PCI_Notify( ) function in the PCI API, the notify( ) method 244 is called for each application to be notified (i.e., an application whose corresponding application object has a relationship with the particular event object that corresponds to the event that is the subject of the PCI_Notify( ) function). For each application, this notify( ) method 244 enqueues the event onto the corresponding i_msgQ_p event queue 266, and signals the i_appEvent NT event object 264 to wake up the NT event thread for that application. This thread then dequeues the event, and calls the notifyApp( ) 246 method which notifies the application.

2.2.3 PCI DataC

Figure 6:
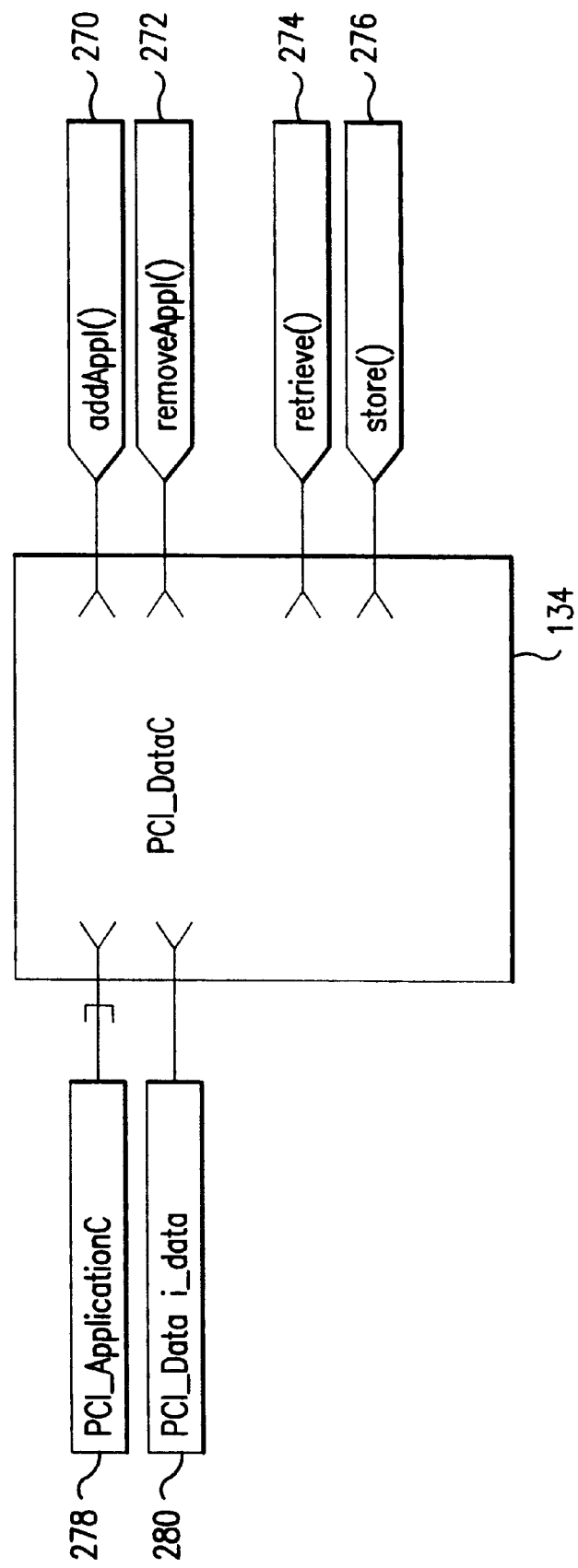
FIG. 6 illustrates the PCI_DataC object class, in particular, class methods and members.

The PCI_DataC class 134 is illustrated in FIG. 6. Each object of class PCI_DataC represents data to be shared between applications; each unique data type registered with the PCI has a PCI_DataC object created for it. These data objects are created by PCI_ApplicationC objects, as described above.

Each PCI_DataC object is identified by the data type ID that is passed by the application when the PCI_RegisterData( ) function is called (see dataID in the description of the PCI_RegisterData( ) function above). When a type of data is shared by two or more applications, each must register the same data type, and the PCI will maintain a single PCI_DataC object for that data type.

Each PCI_DataC object maintains a list of PCI_ApplicationC objects that have registered to access the particular type of data 278. These data users are added and removed by the addAppl( ) 270 and removeAppl( ) 272 methods of the PCI_DataC objects. When an application registers a data type that has not already been registered by any application, that application's PCI_ApplicationC object creates a PCI_DataC object for that data type. When another application registers the same data type, no new PCI_DataC object is created; rather, that second application is added to the list of PCI_ApplicationC objects 278 (which list 278 initially only includes the application that caused the PCI_DataC object to be created) maintained by the PCI_DataC object that has already been created for that data type. This list 278 is used to allow the PCI_DataC object to be referenced by more than one application, while still ensuring that each application doing a store or retrieve has actually registered with the PCI its interest in PCI_Data type.

When an application calls the PCI_Store( ) function to update a data value, the data type is mapped to its PCI_DataC object, and the store( ) method 276 is called. This method stores the value in shared memory in a variable known in the PCI_DataC object as i_data 280, and sends a message to the PCI_PCIC object indicating that a particular type of data has been updated. The PCI_PCIC object then handles this as it does other events for which applications may be registered for notification.

When an application calls the PCI_Retrieve( ) function to retrieve a data value, the data type is mapped to its PCI_DataC object, and the retrieve( ) method 274 is called. This method gets it data value from the variable i_data 280 in shared memory and returns it into the application buffer passed with the PCI_Retrieve( ) call.

When an application terminates, the corresponding PCI_ApplicationC object is deleted and all references to it are removed from the PCI_DataC objects.

2.2.4 PCI EventC and PCI_EventUserC

Figure 7:
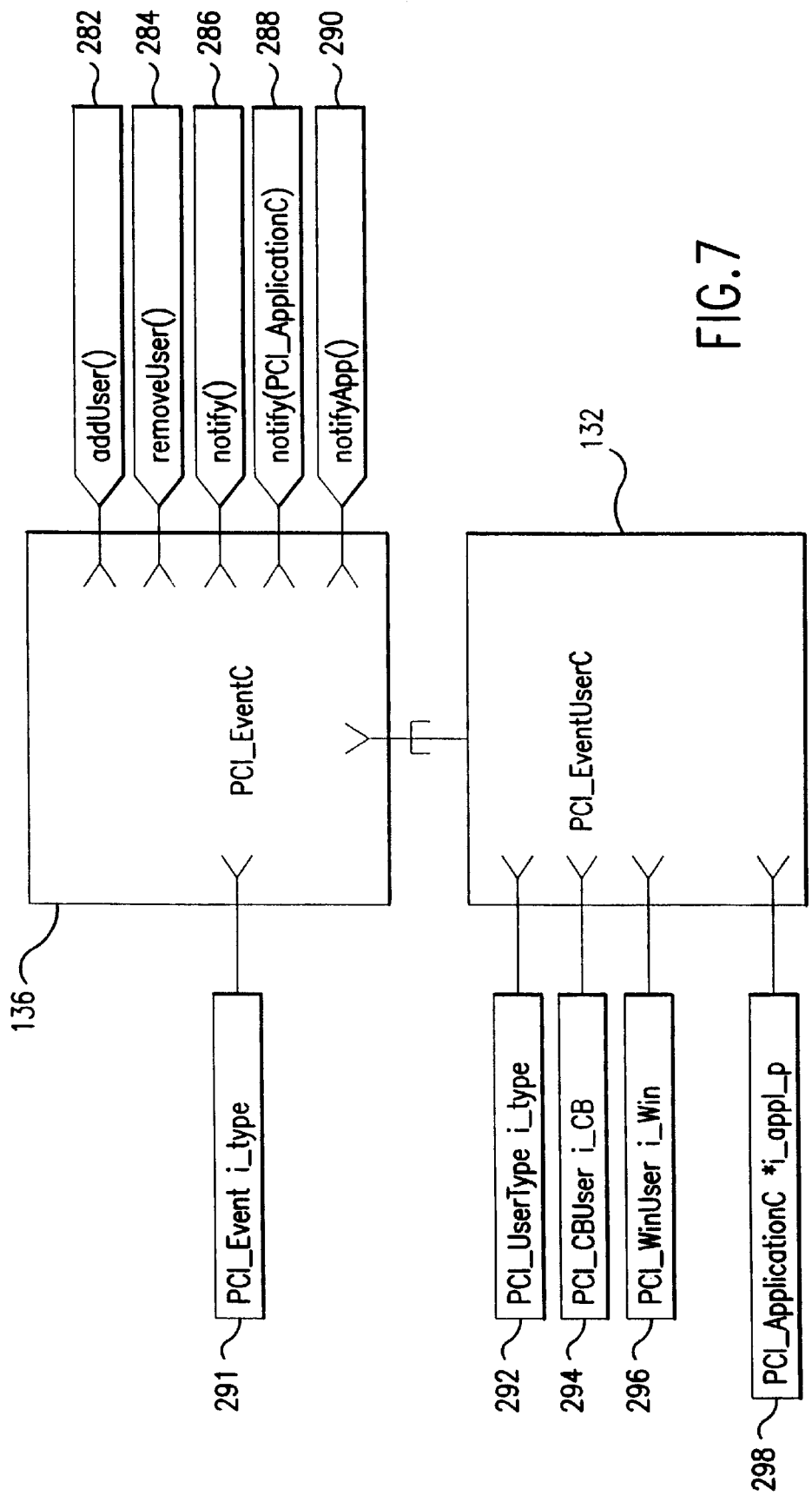
FIG. 7 illustrates the PCI_EventC and PCI_EventUserC object classes, in particular, class methods and members.

Classes PCI_EventC 136 and PCI_EventUserC 132 are illustrated in FIG. 7.

An object of class PCI_EventC is created for each unique event type registered with the PCI. Each object of class models an application defined event in the PCI. Each PCI_EventC object is identified by the event type ID (stored in the objects i_type variable 291) that is passed by the application when the PCI_RegisterEvent( ) or the PCI_RegisterEventW( ) function is called (see eventID in the description of the PCI_RegisterEvent( ) and PCI_RegisterEventW( ) functions above). When a type of event is shared by two or more applications, each must register the same event type, and the PCI will maintain a single PCI_EventC object for that event type.

There is information unique to each application that is needed to notify that application. So that a single PCI_EventC object 136 can be used to handle event notifications for a plurality applications, a PCI_EventC object creates an object of class PCI_EventUserC 132 for each application registering that PCI_EventC object's event type. These PCI_EventUserC objects 132 are added and removed by the addUser( ) 282 and removeUser( ) 284 methods of the corresponding PCI_EventC object.

Thus, there will be one or more PCI_EventUserC objects 132 for each PCI_EventC object 136, with each PCI_EventUserC 132 object encapsulating the information needed to notify a particular application about that type of event (received in the PCI_RegisterEvent( ) and PCI_RegisterEventW( ) function calls). This information is stored in a set of variables: one variable 292 indicates whether the notification is to be via a callback function in the application or by a posting a message to the application's window; a second variable 294 stored the information needed in the case of a callback (e.g., pointer to the function, and the parameters to be passed); a third variable 296 stores the information needed in the case of a window message (e.g., window handle, and the message to be posted).

When an application calls the PCI_Notify( ) function to notify one or more other applications that an event has occurred, the event type is mapped to the corresponding PCI_EventC object, and the notify( ) method 286 for that object is called. This method loops through all the event users in the PCI_EventUserC array and notifies each application the event has occurred. If PCI_Notify( ) specifies a specific application to be notified (see the PCI_ApplHandle hndl parameter in the description of PCI_Notify( ) ), then the notify( ) method is invoked with a parameter identifying the application to be notified (this second version of the notify method is referred to as notify(PCI_ApplicationC) 288 in FIG. 7). When either version of the notify( ) method (286 or 288) is invoked, the notifyApp( ) 290 method is called internally by the PCI to perform the actual application notification; notifyApp( ) 290 method determines which type of event user the application is, and then either calls the application callback procedure or posts a Microsoft Windows message, depending on the type of event user.

When an application terminates, the corresponding PCI_ApplicationC object is deleted and all references to it are removed from PCI_EventC objects by deleting the PCI_EventUserC objects that have references to the PCI_ApplicationC.

2.2.5 PCI QueueC

A PCI_QueueC object is created for each registered application. However, this is an implementation simplification; the PCI_QueueC object could be created at another time, such as when the application registers an event.

Objects of class PCI_QueueC manage the event queues for the PCI, as described above in connection with the PCI_ApplicationC class.

2.2.6 PCI_AllocatorC

Objects of class PCI_AllocatorC manage shared memory and the allocation of objects within shared memory. A single master allocator is created for the entire PCI, and each class described above has its own allocator created for it.

2.3 Event Diagrams

The event diagrams in FIGS. 8–14 show interactions between objects in the illustrative PCI. Event diagrams are an easy way to show object interaction, as well as design the implementation of method calls in a object oriented system. Object classes are labeled at the top of each event diagram; the vertical bar below each label represents an object of the class identified by the label. Each object event is represented by an arrow; the arrow points to the recipient of the event, away from the sender of the event. Above the arrow appears the event name; below the arrow is listed any method (function) in the class that implements the event. The sequence of events is illustrated by the vertical arrangement, with earlier events being above later events.

Note that the "events" illustrated in the event diagrams are part of the operation of the PCI; these are not the "events" that are shared between applications by use of the PCI such as with the PCI_RegisterEvent( ) and PCI_Notify( ) functions.

2.3.1 Application Initialization

Figure 8:
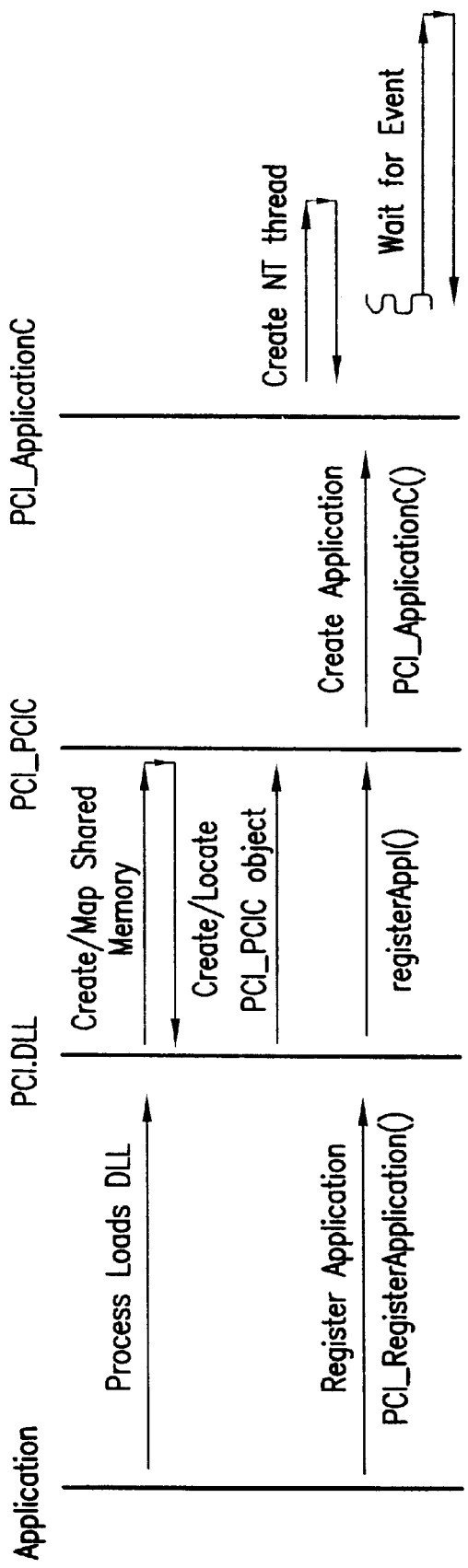
FIGS. 8–14 are event diagrams that show the interaction between objects in the illustrative PCI.

FIG. 8 is an event diagram illustrating an application's initialization of its use of the PCI. This includes the loading by an application of PCI.DLL and registration of the application with the PCI. When a PCI application loads the PCI.DLL, the PCI is initialized and shared memory is either initialized (if first process using the PCI) or is attached to (if not first application). When the application calls the PCI_RegisterApplication( ) function, the PCI creates a PCI_ApplicationC object to model the application, as well as a NT PCI event thread for event notification (alternatively, the PCI could be arranged to create threads only for those applications that actually register events). The event thread then waits until it is signaled that an event has been queued.

2.3.2 Registering Data

Figure 9:
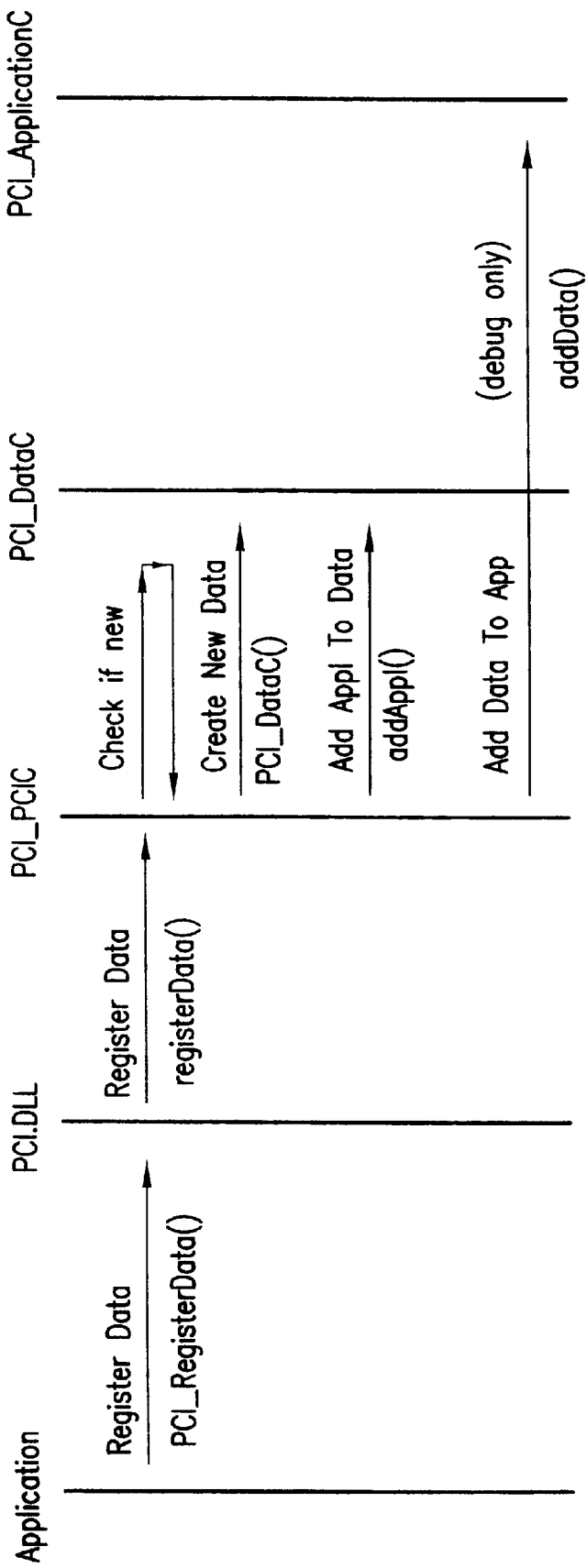

FIG. 9 is an event diagram illustrating registration of data by an application. The application calls the PCI_RegisterData( ) function, which invokes the registerData( ) method of the PCI_PCIC object. If a PCI_DataC object does not already exist for the requested data type, then one is created. The application is added to the list of applications registered for that data type by invoking the addAppl( ) method of the preexisting or newly created PCI_DataC object. For debugging purposes, the addData( ) method is invoked for the PCI_ApplicationC object corresponding to the application, thereby permitting that object to maintain a list of data types for which that application is registered.

2.3.3 Registering Events

Figure 10:
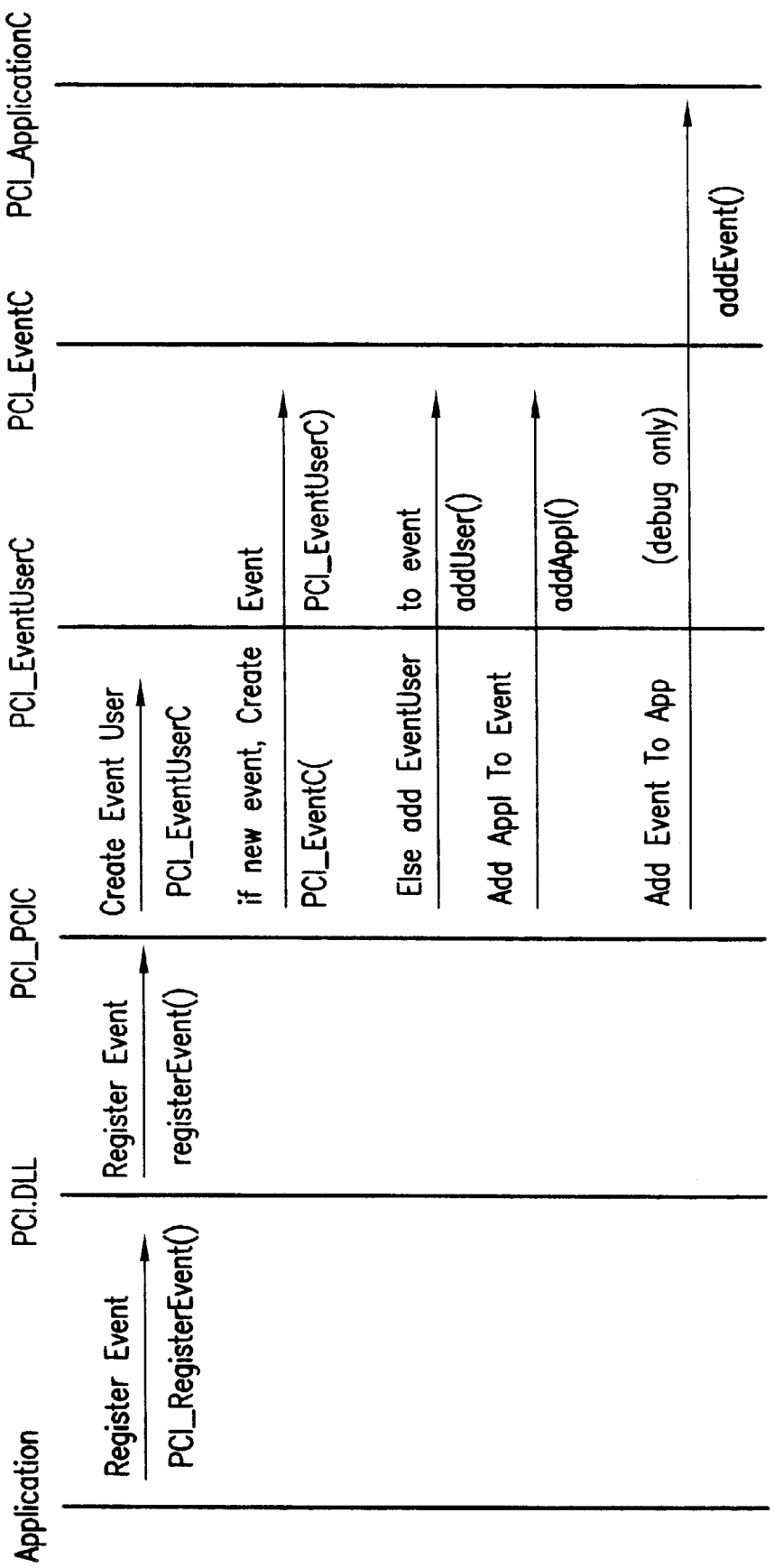

FIG. 10 is an event diagram illustrating registration of an event by an application. The application calls the PCI_RegisterEvent( ) function, which invokes the registerEvent( ) method of the PCI_PCIC object. This creates a new PCI_EventUserC object and, if this is a new event type, creates a PCI_EventC object with a reference to the PCI_EventUserC object; if a PCI_EventC object already exists for this type of event, then its addUser( ) method is called to add a reference to the new PCI_EventUserC object. The PCI_EventC object's addAppl( ) method is also invoked to enable the object to maintain a list of references to the applications that have registered that event (by creating PCI_EventUserC objects, as described above). For debugging purposes, the addEvent( ) method is invoked for the PCI_ApplicationC object corresponding to the application, thereby permitting that object to maintain a list of event types for which that application is registered.

2.3.4 Storing Data

Figure 11:
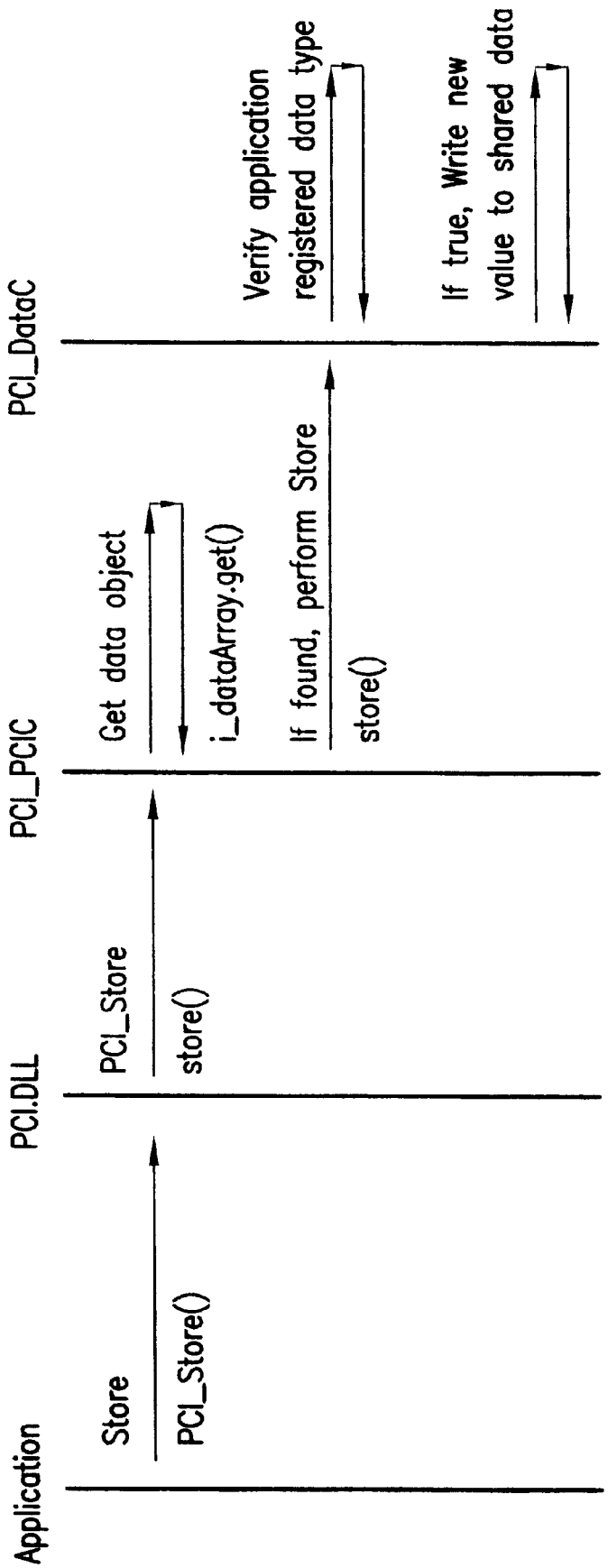

FIG. 11 is an event diagram illustrating an application storing a specific data value into a previously registered data type. The application calls the PCI_Store( ) function, which invokes the store( ) method of the PCI_PCIC object; this identifies the PCI_DataC object for the specified data type. If a PCI_DataC object was identified, then the storeo method for that object is invoked, which verifies that the application requesting the "store" operation is registered for that data type and then actually stores the new data value. The store( ) method also sends a message to the PCI_PCIC object indicating that a particular type of data has been updated, so that any applications registered to be notified of updates to that data item will be notified (as described in connection with FIG. 13).

2.3.5 Retrieving Data

Figure 12:
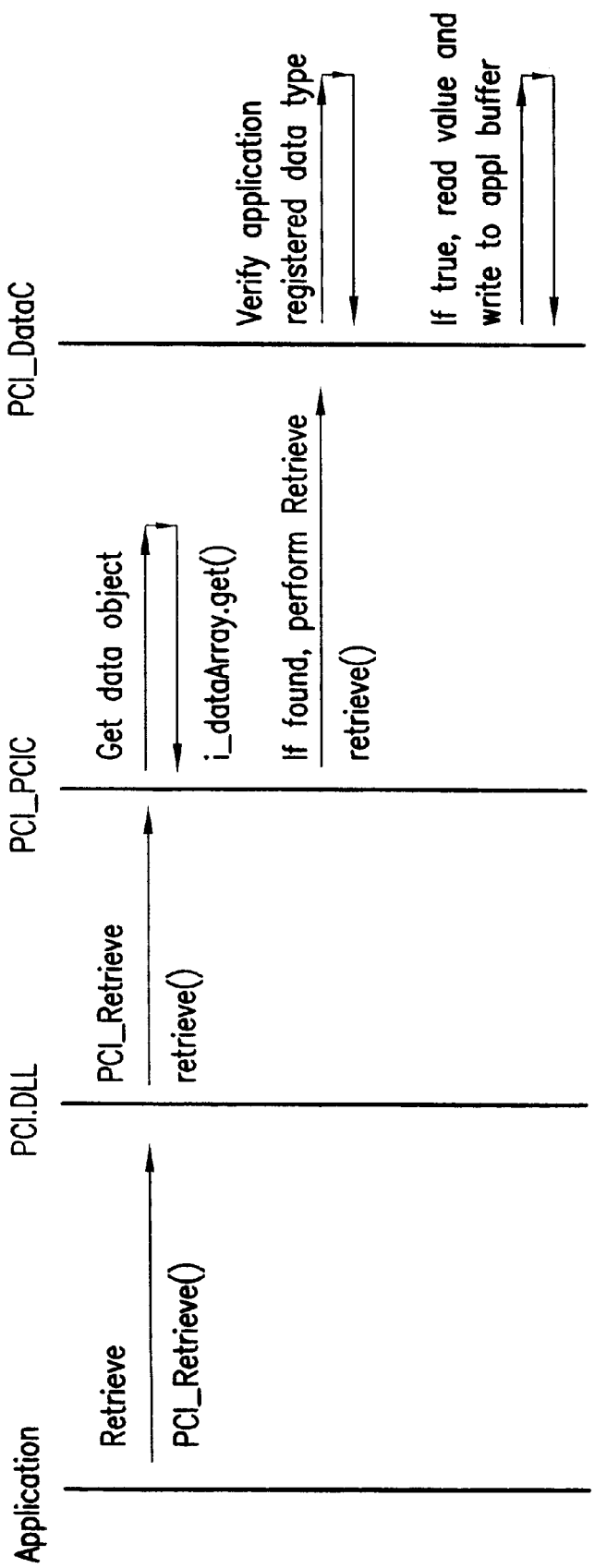

FIG. 12 is an event diagram illustrating an application retrieving a specific data value from a previously registered data type. The application calls the PCI_Retrieve( ) function, which invokes the retrieve( ) method of the PCI_PCIC object; this identifies the PCI_DataC object for the specified data type. If a PCI_DataC object was identified, then the retrieve( ) method for that object is invoked, which verifies that the application requesting the "retrieve" operation is registered for that data type and then actually retrieves the value that was previously stored for that data type.

2.3.6 Event Notification

Figure 13:
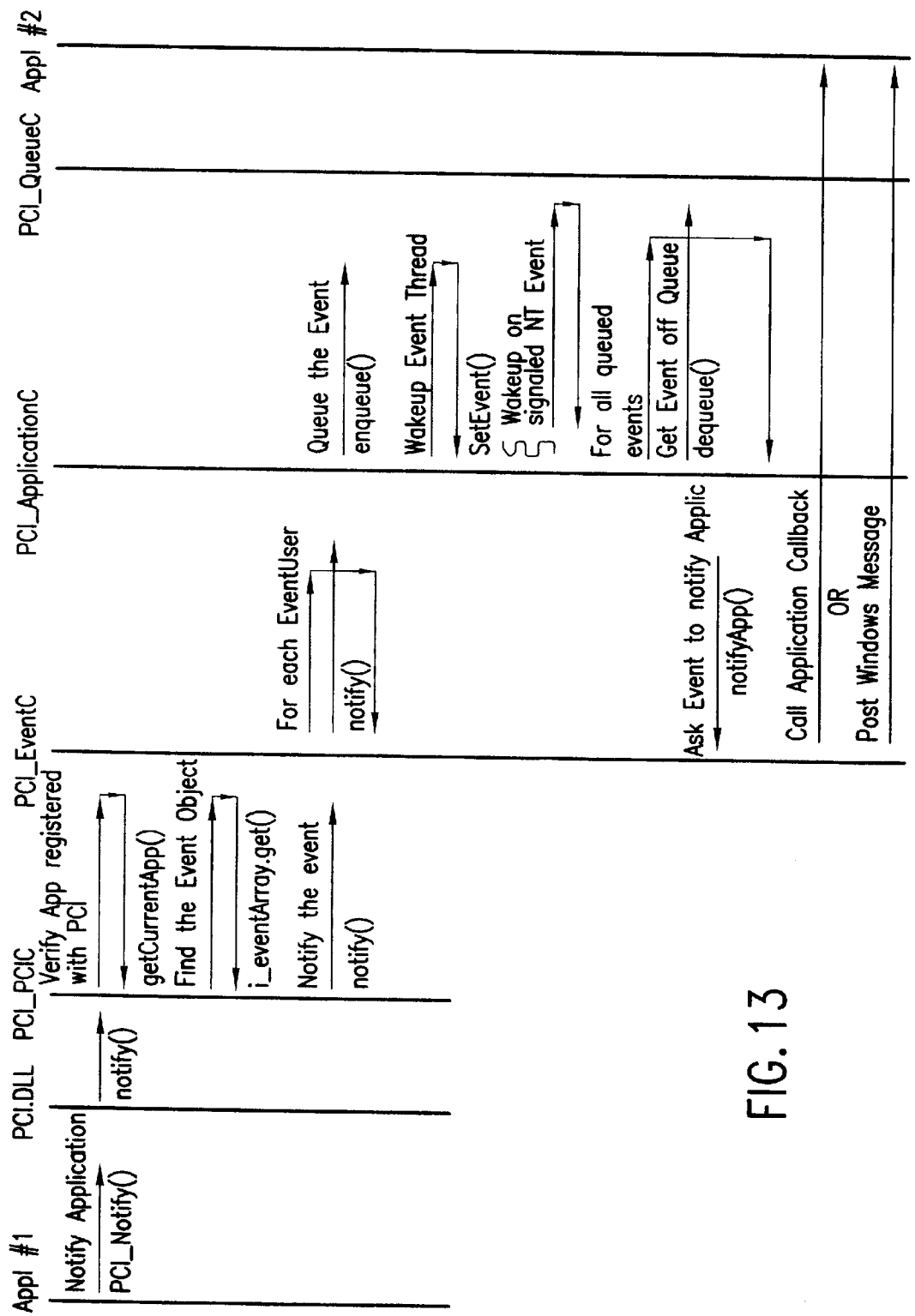

FIG. 13 is an event diagram illustrating a first application notifying second application of an instance of a previously registered event type. The first application calls the PCI_Notify( ) function, which invokes the notify( ) method of the PCI_PCIC object. The PCI_PCIC object verifies that the first application is registered with the PCI, identifies the PCI_EventC object for the type of event that is the subject of this notify operation, and invokes the notify( ) method of that PCI_EventC object. For each PCI_EventUserC object referenced by that PCI_EventC object, the corresponding PCI_ApplicationC object's notify( ) method is invoked. This queues the event (by invoking the enqueue( ) method of the PCI_QueueC object for application being notified) and makes a request (to the corresponding NT event object) to signal the recipient application's event thread (that was created when the application's PCI_ApplicationC object was created) to wake up and process event. When signaled, that thread processes all events in that application's PCI_QueueC object as follows: the event is removed from the queue and the notifyApp( ) method is invoked in the recipient application's PCI_ApplicationC object. The notifyApp( ) method either calls the recipient application's callback function or posts a Microsoft Windows message for the recipient application (depending on whether the application registered for the event using the PCI_RegisterEvent( ) function or the PCI RegisterEventW( ) function).

2.3.7 Application Termination

Figure 14:
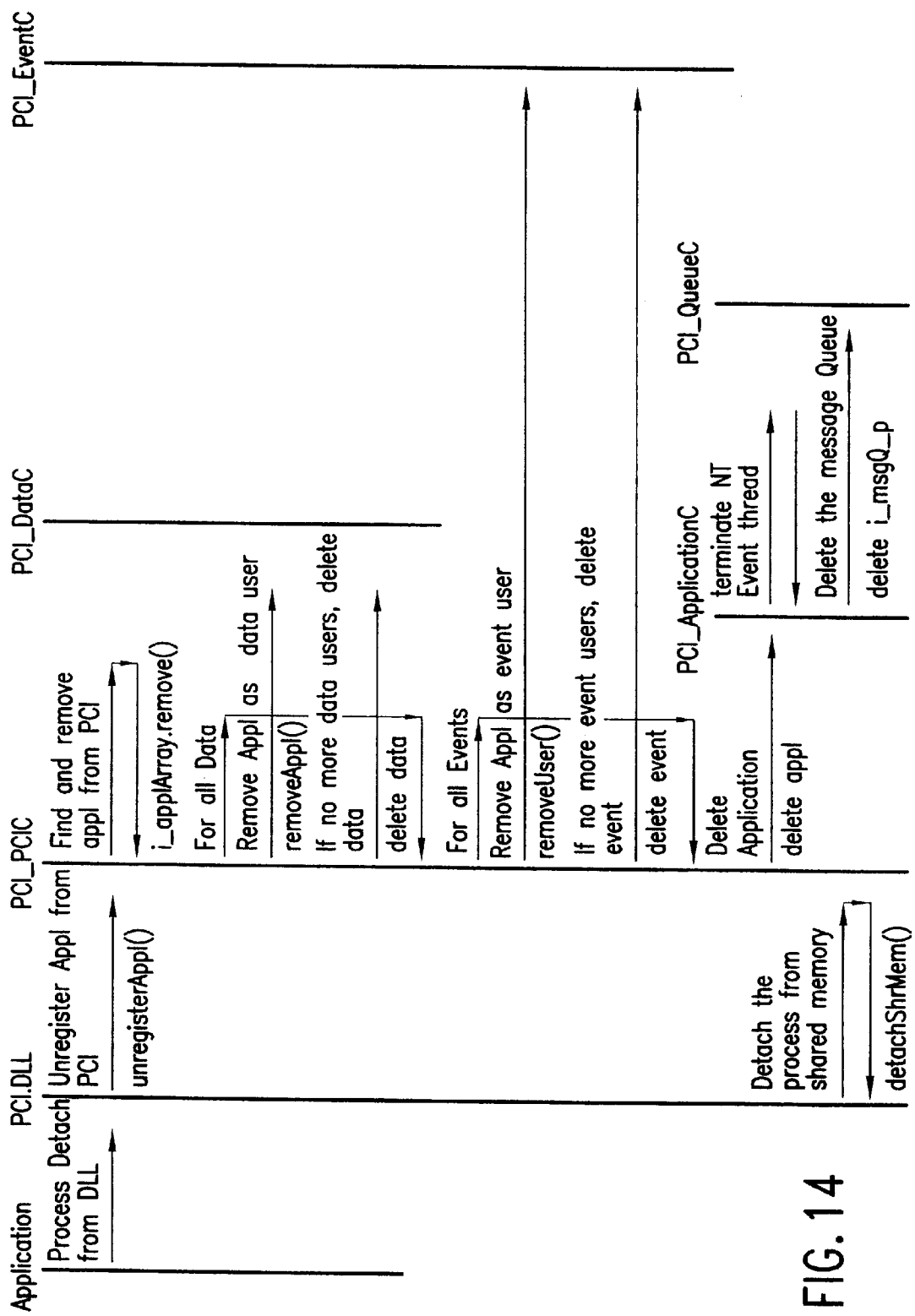

FIG. 14 is an event diagram illustrating termination of an application that has registered with the PCI, causing the unloading of the PCI.DLL. When the application's NT process detaches from the DLL (or when the PCI determines that the application is no longer running), the unregisterAppl( ) method of the PCI_PCIC object is invoked and the process is detached from the shared memory used by the PCI. When any application registers or when the PCI_RetrieveAppls( ) function is called, then the PCI checks to make sure that all registered applications are still rumnning; such checks could be made at other times, but these are two times when accuracy of the list of registered applications is particularly important.

When unregisterAppl( ) is invoked, the PCI_PCIC object removes that application from the list of applications registered with the PCI, removes the application as a registered user of any data types or event types for which the application had registered (and deletes the corresponding data and event objects if in cases where there are no more registered applications for the corresponding data type or event type), and deletes the application's PCI_ApplicationC object (including terminating the NT event thread created for that application and deleting the PCI_QueueC object created for that application).

2.4 Miscellaneous

The ability to send events between applications is implemented as an event queue that feeds a separate NT thread for each application registering with the PCI. When an application calls the PCI_Notify( ) function, the event is placed on the event queue of the application to be notified. The PCI NT thread for this notified application is signaled to read the event off the queue and notify the application. The notification occurs in one of two ways depending upon which register event function was called—PCI_RegisterEvent( ) or PCI_RegisterEventW( ). The first method notifies the application by having the PCI NT thread call an application callback. The second method notifies the application by having the NT thread post a message to the application's Microsoft Windows message queue.

Applications that are not native NT applications (i.e., 16-bit Microsoft Windows 3.1 applications) use the 16-bit interface to the PCI, known as PCI16.DLL. This interface converts all application data passed to the PCI functions from 16 bit to 32 bit values, as well as from the 16-bit segmented memory model to the 32-bit flat memory model. Under NT this conversion is known as "thunking", and the PCI16.DLL interface is known as a "thunking layer".

To expedite implementation of the PCI, the illustrative embodiment has the following limitations:

| PCI.h constant | value |
|---|---|---|
| maximum number of applications that can be registered at one time | PCI_APPLMAX | 10 |
| maximum application name length | PCI_APPLNAMEMAX | 25 |
| maximum number of data types that can be registered at one time | | 20 |
| maximum number of event types that can be registered at one time | | 20 |

3 Developing Context Sharing Applications

3.1 The Mechanics

An application developer can use the following steps to create application programs to take advantage of the PCI:

1. Create a common header file to be used by all of the applications wishing to share data and events through the PCI. In this header file, include the PCI header file PCI.h. Define the PCI_Data and PCI_Event types to be shared by the applications in the common header file.

2. Create the application code that interacts with the PCI. This code includes calls to various PCI functions, including functions that register certain information about the application with the PCI, and functions that implement the sharing of data and/or events with other applications. Before calling other PCI functions, an application must register (i) itself, (ii) all data types that it will supply or receive, and (iii) all event types that it will supply or receive with the PCI. The order in calling the PCI functions should be:

PCI_RegisterApplication( <application name> )

PCI_RegisterData( <data type defined in common header file> )

PCI_RegisterEvent( <event type defined in common header file> )

Any other PCI function, i.e. PCI_Store( ), PCI_Retrieve( ), PCI_Notify( ), etc.

3. Compile the application programs.
4. Link each application, using the PCI16.lib (that includes functions for accessing PCI16.DLL) if it is a 16-bit application, or using the PCI.lib (that includes functions for accessing PCI.DLL) if it is a 32-bit application.
5. At runtime insure the PCI.DLL (and PCI16.DLL if using 16 applications) is in the "path" or is in the NT system32 directory. In order to run multiple 16 bit PCI applications or different instances of the same 16 bit applications insure each instance is started in its own NT Virtual DOS Machine (NTVDM). This can be done by issuing the following command at an NT console:

>start /separate <program name>

To aid in debugging applications that interact with the PCI, the illustrative embodiment includes two tools. These tools are separate from the PCI, but interact with it.

A tool known as 'pcimon.exe' presents a console that displays information about PCI activity. Its operation is illustrated by a sample of its displayed output:

D:\tempchamsys\chameleon\PCI\src\pci_DLL.cpp 1151
DEBUG:
Registered Application pcimon.exe214209

PCI_Debug: Event Occurred, EventId 1 DataId 0
New appl registered

PCI_Debug: New PCI DataType added, DataId 256

PCI_Debug: PCI Data Changed, DataId 256
This is a great test of the PCI

PCI_Debug: Event Occurred, EventId 257 DataId 0
Focus Change Event

PCI_Debug: Event Occurred, EventId 4 DataId 0
Application unregistered

Another tool, known as 'pcitst16.exe', is a 16-bit Microsoft Windows program (run in a separate NTVDM) which allows a user to store MRN values, to send Focus Change events, and to view the names of applications registered with the PCI.

3.2 PCI.h

The following is the C language header file PCI.h for use in compiling applications to be used with the illustrative embodiment of the PCI:

```
#ifndef _PATIENTCONTEXT_INTERFACE_H
#define _PATIENTCONTEXT_INTERFACE_H
/* -*-C-*-
****************************************************************
*
* File:         PCI.h
* Description:  Common header file for using the Patient Context
*               Interface. Defines all typedefs, constants, and function
*               prototypes needed to interact with the Interface.
* Language:     C
* Subsystem:    PCI
*
****************************************************************
*/
#ifdef __cplusplus
extern "C"
{
#endif
#ifdef _PCI_DEBUG_
#define PCI_API
#else
#ifdef _NT_
```

-continued

```
#ifdef NODECLSPEC
#define PCI_DECL
#else
#define PCI_DECL __declspec( DLLimport )
#endif
#define PCI_API
#else
// 16 bit windows
#define PCI_DECL
#define PCI_API  far
#endif
#endif
// Typedefs
typedef unsigned char u1b;
typedef signed long s4b;
typedef unsigned long u4b;
typedef s4b PCI_ReturnType;
typedef u4b PCI_DataType;
typedef u4b PCI_EventType;
typedef void PCI_API *PCI_Any;
typedef u4b PCI_DataSz;
typedef u4b PCI_UMsg;
typedef u4b PCI_ApplHandle;
typedef u1b PCI_ApplIndex;
typedef u4b PCI_HWND;
typedef struct _PCI_Data
{
    PCI_DataType dataId;
    PCI_Any datap;
    PCI_DataSz sz;
}PCI_Data;
typedef struct _PCI_Event
{
    PCI_EventType eventId;
    PCI_DataType optDataId;
}PCI_Event;
typedef PCI_ReturnType ( *PCI_InterfaceCB )( PCI_Event event,
    PCI_Any clientDatap );
// Valid Return Types
#define PCI_SUCCESS          0x00000000
#define PCI_ERROR            0x00000001
#define PCI_DUPLICATEAPP     0x00000002
#define PCI_MAXREACHED       0x00000003
#define PCI_EVENTSETERROR    0x00000004
#define PCI_EVENTRESETERR    0x00000005
#define PCI_BUFFER2SMALL     0x00000006
#define PCI_INVALIDDATA      0x00000007
#define PCI_NOTREGISTERED    0x00000008
#define PCI_NODATA           0x00000009
#define PCI_INVALIDARGS      0x0000000a
#define PCI_INVALIDHNDL      0x0000000b
// Supported DataTypes
#define PCIDATA_RESERVED 255
enum { PCIData_Null    = 0,
       PCIData_MRN     = PCIDATA_RESERVED + 1
     };
// The below value defines the size of a patients MRN, which is a 20
// character string ( + 1 for NULL ). Each application should define and
// register a PCI_Data as:
// char buff[PCIData_MRNLength]:
// PCI_Data appl_MRN = { PCIData_MRN, &buff,
// PCIData_MRNLength };
#define PCIData_MRNLength   21    // includes NULL character
// Supported Events
#define PCIEVENT_RESERVED 255
enum { PCIEvent_Null         = 0,
       PCIEvent_DataChange   = PCIEVENT_RESERVED + 1,
       PCIEvent_FocusChange  = PCIEVENT_RESERVED + 2 };
const PCI_Event PCI_EventStruct_Null = { PCIEvent_Null,
PCIData_Null };
//
// Application handle meaning all applications
//
#define PCI_ALLAPPLICATIONS     0xffffffff
#define PCI_APPLNAMEMAX         25
#define PCI_APPLMAX             10
//
// Function Prototypes for interacting with the Interface
//
```

-continued

```
// Maximum application name is 25 characters, including NULL
PCI_DECL PCI_ReturnType PCI_API PCI_RegisterApplication( char
     PCI_API *name );
PCI_DECL PCI_ReturnType PCI_API PCI_RegisterData( PCI_Data
     data );
PCI_DECL PCI_ReturnType PCI_API PCI_RegisterEvent( PCI_Event
                                                      event,
                                                 PCI_Any clientDatap,
                                                 PCI_InterfaceCB
                                                      notifyCallBack );
PCI_DECL PCI_ReturnType PCI_API PCI_RegisterEventW( PCI_
                                                      Event event,
                                                 PCI_HWND window,
                                                 PCI_UMsg uMessage );
PCI_DECL PCI_ReturnType PCI_API PCI_Notify( PCI_Event event,
                                                 PCI_ApplHandle hndl );
PCI_DECL PCI_ReturnType PCI_API PCI_RetrieveAppls(
              char PCI_API* PCI_API*namev,
              PCI_ApplHandle PCI_API *PCI_API *hndlv,
              PCI_ApplIndex PCI_API *count );
PCI_DECL PCI_ReturnType PCI_API PCI_Retrieve( PCI_Data data );
PCI_DECL PCI_ReturnType PCI_API PCI_Store( PCI_Data data );
#ifdef __cplusplus
} /* extern "C" */
#endif
#endif   /* PATIENTCONTEXT_INTERFACE_H */
```

3.3 Use of the PCI API

Computer systems provide various generic mechanisms for users to switch from one application to another. For example, the illustrative embodiment of the invention runs on Microsoft's NT operating systems, from which a user can switch to an application in various ways, including by launching the application from the NT program manager and by selecting the icon representing a minimized (previously launched) application.

In addition to such generic mechanisms provided by the computer system, applications can themselves provide mechanisms for switching directly to other applications. For example, an application may provide a button or menu selection to switch to another frequently used application.

The illustrative PCI embodiment provides a mechanism for changing the system focus from one running application to another running application. It does not provide a mechanism for launching an application—i.e., starting an application running. However, it could be extended to include the ability to launch applications. For example, the PCI could include an API function to launch any of a predefined set of applications (based on information stored in the PCI about how to launch these applications—such as all of the patient information applications that are available to run on that computer system); also, it could include an API function to launch any application, as long as the application provides the information needed to effect the launch (typically, this API function would be unnecessary as such function would already be available from the computer system's operating system software).

When an instance of an application is already running, and the user desires to switch to that application, typically, the users expects to switch to the instance that is already running. However, there are some cases where it is desirable to launch a new instance of the application; the choice of whether to switch the focus to the existing instance or to a newly launched instance depends on the use model for that particular type of application and data.

3.3.1 What Happens When an Application Receives an Event?

An application that receives notification of an event from the PCI takes action that depends upon the type of event and the nature of that application.

For example, consider the case where the user is working with one patient's data in a clinical information charting application, and a laboratory data application also has a window open that is also visible to the user. When the user selects a different patient in the charting application, that application updates the MRN stored in the PCI (by using the PCI_Store( ) function). The PCI automatically notifies the laboratory data application that the MRN has changed. If the laboratory data application is displaying patient data, then that application will use the PCI_Retrieve( ) function to obtain the updated MRN value and then change the data that it displays so that it displays data for the patient identified by the retrieved MRN. Thus, the user sees data for the same patient in both the charting window and in the laboratory data window. If, instead, the laboratory data application was not displaying anything that was specific to a particular patient, it would not need to update its display in response to the MRN change event.

One type of event that is predefined in the PCI is a focus change event. A focus change event is sent by one application to another application (via the PCI using PCI_Notify( )) to change the user interface focus to the recipient application. When an application receives a focus change event from the PCI, that recipient application takes action to obtain the focus; for example, the application may make an NT system call to have its window "maximized", which will result in the application receiving the user interface focus. There are various other actions that an application can take that will also result in the application receiving the focus.

3.3.2 What Happens When Switching Applications?

For user efficiency (e.g., due to the typical use model, it may be more efficient for certain application switches to be handled differently from others) or for ease of implementation (it may be more difficult to detect and react properly to certain types of application switch mechanisms) an application may be designed to react differently depending on how it is "switched to". However, typically, an application would be designed to react to being "switched to" in the same manner, no matter how the user achieves the switching.

When switching to an application being launched, the newly launched application should select the patient specified in the PCI. However, switching to an application when it is already running requires consideration of a number of different situations, depending on the state of the running application. In general, the behavior of the switched-to application should facilitate common sequences of user operations, and do so while avoiding user confusion. The following is an example of how an application such as Hewlett-Packard's CareVue clinical information system might be designed to react to being "switched to".

If there is no patient context information in the PCI, then the running application is simply maximized. In some cases (some states of the application being switched to) it may be appropriate to set the application to a main menu; in other cases it may be appropriate to simply leave the application at the point where it was prior to being maximized.

If there is patient context information in the PCI and no patient is selected in the running application, then the application is maximized and the patient specified in the PCI is selected.

If there is patient context information and the same patient is already selected in the application, then the application is simply maximized—the state of the application is not changed (i.e., the application is not re-started with that patient).

If there is patient context information, a different patient is selected, and the application is in data entry mode, then display a warning message indicating that the patient selection is not automatically changed when in data entry mode (this is to avoid the loss of any data that may not have been stored for the patient that was selected in the application at the time of the "switch-to" operation).

If there is patient context information, a different patient is selected, and the application is not in data entry mode, then maximize the application and select the patient identified by the PCI.

Also, to avoid loss of data being entered, when an application is in data entry mode, the switch-to option would not typically be made available. In other words, the user would be required to store any entered data before using the switch-to operation to switch to another application.

When the patient specified by the patient context is not located by the "switched to" application, typically, that application should present a mechanism by which the user can select a patient.

3.3.3 Switch-to Menu

As mentioned above, one mechanism for switching applications is that an application can provide menu selections or buttons for switching to other applications. An application may make these switching mechanisms available on a selective basis. For example, when an application is in data entry mode, the switch-to mechanisms may not be made available until the user stores the data being entered—to make sure that the unstored data is not lost.

Further, these switch-to mechanisms can be made dynamic in content by use of the PCI. An application can use the PCI_RetrieveAppls( ) function to obtain a list of those applications that have registered with the PCI, and can create menu with a switch-to selection for each of the currently registered applications. (Alternatively, these switch-to selections may be added to an existing menu, or may be provided in the form of buttons or other user interface device.)

A user of such application can select a switch-to menu option (or other device, such as a button), which then results in display to the user of a submenu that lists the applications that are currently registered with the PCI. The user then selects an application from the submenu. The application that presented the submenu then sends a focus change event through the PCI to the selected application and minimizes itself.

The switch-to capability could be extended to include applications in addition to the ones that are running and have registered with the PCI. If the PCI is extended to include the ability to launch particular applications, then these "launchable" applications could be included in the list of registered applications, or the PCI could include an additional API that provides a list of the applications that it can launch. In either case, an application could then include on its switch-to menu these additional applications, even though they are not currently running. Further, an application could be programmed with the ability to launch particular applications itself, and it could add these to its switch-to menu.

Figure 15:
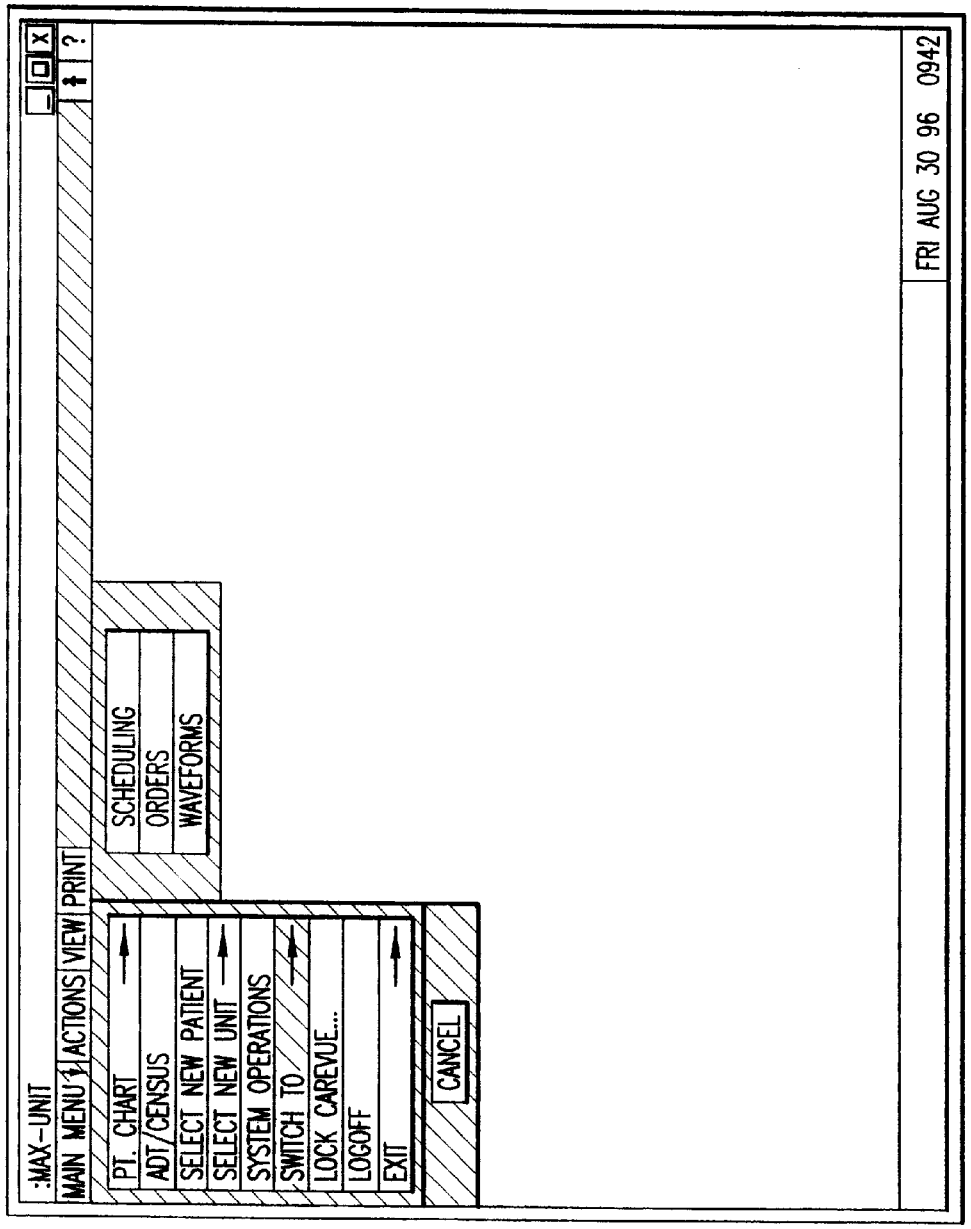
FIG. 15 is a screen display illustrating a "switch-to" menu.

FIG. 15 illustrates a screen display of an application with a switch-to submenu. There is a menu bar (options "Main Menu", "Actions", "View", and "Print") from which the "Main Menu" has been selected and is displayed (with these options: "Pt. Chart", ADT/Census", "Select New Patient", "Select New Unit", "System Operations", "Switch To", "Lock CareVue . . . ", "Logoff", "Exit", and "Cancel" the main menu selection). On the Main Menu, the "Switch To" option has been selected. The Switch To submenu is displayed, from which a user can select any of three different applications to which the user interface focus is to be switched (options "Scheduling", "Orders", "Waveforms").

The foregoing has described a specific embodiment of the invention. Additional variations will be apparent to those skilled in the art. For example: although the invention has been described in the context of an object-oriented implementation running on Microsoft Windows NT, it can be implemented in other operating system environments and using other programming techniques; the internal implementation of the PCI and the function calls and parameters used in the API could be organized in other ways. Thus, the invention is not limited to the specific details and illustrative example shown and described in this specification. Rather, it is the object of the appended claims to cover all such variations and modifications as come within the true spirit and scope of the invention.

We claim:

1. A medical information system comprising:
   (A) a patient context interface comprising:
      (1) shared memory means for storing a patient identification;
      (2) means for responding to a first type of service request from an application program by registering that application program as one to which notification is to be sent when the stored patient identification is updated;
      (3) means for responding to a second type of service request from an application program by
         (i) storing a patient identification that is provided by that application program, and
         (ii) notifying each application program that has registered to be notified of updates to be the stored patient identification that such a change has occurred;
      (4) means for responding to a third type of service request from an application program by retrieving the previously stored patient identification and providing it to that application program;
      (5) means for notifying one application program of a focus change event in response to a request from another application program;
   (B) a first application program storing data about patients using an organization that provides for retrieval and display of patient data associated with a patient identification, this first application program being configured to use the second type of service request to store a patient identification corresponding to data being displayed by the first application program, this first application program further includes a mechanism for presenting the user with an application switching option, and a mechanism responsive to the user selecting the application switching option for requesting that the patient context interface send a focus change event to another application program; and
   (C) a second application program storing data about patients using an organization that provides for retrieval and display of patient data associated with a patient identification, this second application program being configured to use the first type of service request and for responding to notification of changes in the stored patient identification by using the third type of service request to retrieve the stored patient identification and to retrieve and display data associated with the retrieved patient identification, the second application program further includes a mechanism for receiving a focus change event from the patient context interface, obtaining the user interface focus, requesting that the patient context interface provide a patient identification, and retrieving and displaying data for the corresponding patient.

2. A method for switching the user interface focus of a medical information system from a first application program to a second application using a patient context interface service program and maintaining continuity of patient context comprising:

(A) the first and second application programs each registering with the patient context interface service program;

(B) the first application program sending a patient identification corresponding to data being displayed by the first application program to the patient context interface service program;

(C) the patient context interface service program storing the patient identification;

(D) the first application program generating a service request for retrieving from the patient context interface service program a list of application programs that have registered with the patient context interface service program;

(E) the first application program sending to the patient context interface service program a request to send a focus change event to the second application program;

(F) the patient context interface service program sending a focus change event to the second application program; and (G) the second application program receiving the focus change event, becoming the user interface focus, retrieving the stored patient identification from the patient context interface service program, and retrieving and displaying patient data corresponding to that patient identification; whereby the user interface focus is switched from the first application program to the second application program with continuity of patient context.

3. An interface for sharing patient context information, including patient identification information, among a plurality of application programs that provide for display of data about particular patients, the interface comprising:

a shared memory storing patient context information; and an interface program through which the plurality of application programs update and obtain patient context information by issuing service requests, the interface program performing the following functions:

responding to a first type of service request by registering the application program that issued the first type of service request;

responding to a second type of service request from a registered application program by storing updated patient context information that is provided by the application program that issued the second type of service request and notifying each registered application program of the updated patient context information; and responding to a third type of service request from a first registered application program to which focus is being switched by retrieving stored patient context information currently being used by a second registered application program and providing the stored patient context information to the first registered application program so that the first application program can display data for the same patient that was displayed by the second application program thereby maintaining continuity of patient context.

4. The interface, as set forth in claim 3, wherein the interface program further performs the following function:

responding to a fourth type of service request by providing a list of registered application programs to which focus can be switched while maintaining continuity of patient context.

5. A healthcare information system comprising:

a patient context interface program that controls access to centrally stored patient context information and provides applications with an indication of which patient's patient context information is currently being used by an application that is currently the focus of a user; and at least two application programs, each application program performing a healthcare related function using a sub-set of patient data including a patient context, each application program upon start up or becoming the focus of a user requesting the patient context interface program to provide patient context information so that the application program can retrieve and display data for the same patient that was displayed by the application program that previously was the focus of the user so as to maintain continuity of patient context.

6. The interface, as set forth in claim 5, wherein the interface program further maintains a list of all application programs for which the interface program controls access to the centrally stored patient context information; and wherein an application program having focus can request a list of application programs from the interface program to which focus can be switched while maintaining continuity of patient context.

* * * * *